(12) United States Patent
De Groot et al.

(10) Patent No.: US 8,945,611 B2
(45) Date of Patent: Feb. 3, 2015

(54) ARTIFICIAL OXYGEN CARRIERS AND USE THEREOF

(75) Inventors: Herbert De Groot, Düsseldorf (DE); Christian Mayer, Duisburg (DE); Frank Petrat, Essen (DE); Michael Kirsch, Hilden (DE)

(73) Assignee: Universität Duisburg-Essen, Essen (DE)

( * ) Notice: Subject to any disclaimer, the term of this patent is extended or adjusted under 35 U.S.C. 154(b) by 378 days.

(21) Appl. No.: 13/003,400

(22) PCT Filed: Jul. 8, 2009

(86) PCT No.: PCT/EP2009/004925
§ 371 (c)(1),
(2), (4) Date: May 4, 2011

(87) PCT Pub. No.: WO2010/003647
PCT Pub. Date: Jan. 14, 2010

(65) Prior Publication Data
US 2011/0223243 A1    Sep. 15, 2011

(30) Foreign Application Priority Data

Jul. 9, 2008 (DE) .................... 10 2008 032 183
Aug. 30, 2008 (DE) .................... 10 2008 045 152

(51) Int. Cl.
*A01N 1/02* (2006.01)
*A61K 9/00* (2006.01)
*A61K 9/16* (2006.01)
*A61K 9/50* (2006.01)
*A61K 9/51* (2006.01)
*A61K 31/755* (2006.01)

(52) U.S. Cl.
CPC ............. *A61K 9/0026* (2013.01); *A01N 1/02* (2013.01); *A01N 1/0226* (2013.01); *A61K 9/1647* (2013.01); *A61K 9/5031* (2013.01); *A61K 9/5153* (2013.01); *A61K 31/755* (2013.01)

USPC ........................................................ 424/451

(58) Field of Classification Search
None
See application file for complete search history.

(56) References Cited

U.S. PATENT DOCUMENTS 5,490,986 A * 2/1996 Speaker .................. 424/451
2008/0213355 A1 * 9/2008 Bohmer ................... 424/451

FOREIGN PATENT DOCUMENTS

WO    WO2007134304   * 11/2007  ............... C01D 1/32

OTHER PUBLICATIONS

Perfluorodec-5-ene [online] retrieved on Mar. 27, 2013 from: http://www.chemicalbook.com/ChemicalProductProperty_US_CB1453544.aspx.*
Perfluorooctyly bromide [online] retrieved on Mar. 27, 2013 from: http://www.chemicalbook.com/ChemicalProductProperty_EN_CB5409529.htm.*
Spahn et al. (Anethesiology 1999, 91, 1195-1208).*
Romich (Fundamentals of Pharmacology for Veterinary Technicians 2005, Cengage Learning, 412 pages; p. 302).*
Pisani et al. (Langmuir 2006, 22, 4397-4402).*

* cited by examiner

Primary Examiner — Ernst V Arnold

(57) ABSTRACT

The invention relates to dispersions of artificial oxygen carriers, wherein the dispersions contain capsules with reversible oxygen storage capacity, the capsules comprising an oxygen-permeable capsule material, that contains and/or encloses fluorinated, particularly perfluorinated hydrocarbons, preferably perfluorocarbons. The dispersions are particularly suitable as a blood substitute, preferably for the purpose of transfusion, e.g. in states of blood loss of the human or animal body, in particular following surgical interventions, accidents, injuries etc, or for the prophylactic treatment and/or treatment by therapy of ischaemic states or states following a reperfusion.

15 Claims, No Drawings

ARTIFICIAL OXYGEN CARRIERS AND USE THEREOF

CROSS-REFERENCES TO RELATED APPLICATIONS

This application is a National Stage filing of International Application PCT/EP 2009/004925, filed Jul. 8, 2009, entitled "ARTIFICIAL OXYGEN CARRIERS AND USE THEREOF" claiming priority to German Applications No. DE 10 2008 032 183.4 filed Jul. 9, 2008, and DE 10 2008 045 152.5 filed Aug. 30, 2008. The subject application claims priority to PCT/EP 2009/004925, and to German Applications No. DE 10 2008 032 183.4, and DE 10 008 045 152.5 and incorporates all by reference herein, in their entirety.

BACKGROUND OF THE INVENTION

The present invention relates to the field of artificial oxygen carriers, particularly as blood substitutes for the human or animal body. In particular, the present invention relates to artificial oxygen carriers based on capsules containing perfluorinated hydrocarbons, particularly nanocapsules.

The present invention particularly relates to artificial oxygen carriers in the form of dispersions that are particularly suitable as blood substitutes for the human or animal body, preferably for the transfusion purposes.

The present invention further relates to the use of these dispersions particularly as blood substitutes for the human or animal body, particularly for transfusion purposes, for example for treating states of blood loss, ischaemic conditions and conditions following reperfusion, and also for other purposes.

The present invention further relates to the use of fluorinated, perfluorinated, hydrocarbons, preferably perfluorocarbons, as artificial oxygen carriers for treatment of the human or animal body, particularly as blood substitutes, preferably for purposes of transfusion or other applications.

Finally, the present invention relates to the use of capsules, particularly nanocapsules, comprising an oxygen-permeable capsule material that contains and/or encloses fluorinated, particularly perfluorinated hydrocarbons, preferably perfluorocarbons, as artificial oxygen carriers, particularly as blood substitutes, but also for other applications.

Blood that is suitable for use in transfusions is a scarce commodity. Blood transfusions are often life-saving operations for accident victims, during surgical procedures, and in the treatment of chronic anaemia. The availability of conserved blood is becoming more and more limited for a number of reasons including infection risks (for example by HIV, prions, hepatitis A, B or C, and others) and falling numbers of people willing to donate blood (see for example Habler, O., Pape, A., Meier, J., und Zwissler, B. (2005) [Artificial oxygen carriers as an alternative to blood transfusion]. Anaesthesist 54, 741-754, and Lowe, K. C. (2006) Blood substitutes: from chemistry to clinic. J Mat Chem 16, 4189-4196).

Moreover, there is increasing evidence to indicate that the function of conserved blood deteriorates markedly, and is demonstrable after just a few days (see for example Riess, J. G. (2001) Oxygen carriers ("blood substitutes")—raison d'etre, chemistry, and some physiology. Chem Rev 101, 2797-2920; Bennett-Guerrero, E., Veldman, T. H., Doctor, A. Telen, M. J., Ortel, T. L., Reid, T. S., Mulherin, M. A., Zhu, H., Bück, R. D., Califf, R. M., und McMahon, T. J. (2007) Evolution of adverse changes in stored RBCs. Proc Natl Acad Sci USA 104, 17063-17068; also Reynolds, J. C., Ahearn, G. S., Angelo, M., Zhang, J., Cobb, F., und Stamler, J. S. (2007) S-nitrosohemoglobin deficiency: a mechanism for loss of physiological activity in banked blood. Proc Natl Acad Sci USA 104, 17058-17062).

Blood transfusions are medical procedures that are carried out very frequently. The supply of oxygen to the organs is by far the most important single function that blood performs; if this supply fails, the victim dies very rapidly. Therefore, the first task in the event of significant blood loss is to ensure the transport of oxygen. This is achieved routinely by the use of erythrocytes from donated blood; these cells contain the protein haemoglobin, which binds oxygen very effectively and releases it to the tissue. However, donated blood is associated with several significant disadvantages: there are not enough donors, and not every recipient can receive any donated blood (incompatibility).

Blood may contain unknown infectious materials (for example viruses among others). Screening for dangerous pathogens is complicated and expensive. And donated blood can only be stored for a limited time.

One efficient solution to this problem is the development of artificial oxygen carriers, which render the use of conserved blood unnecessary, or at least reduce the number of blood transfusions substantially.

Accordingly, research has been conducted for several decades into suitable synthetic substitutes—on the one hand into the use of modified haemoglobin and on the other into the use of perfluorinated hydrocarbon (perfluorocarbons), which have very good binding and releasing properties in respect of oxygen.

Besides the oxygen carriers based on haemoglobin derivatives—the development of which has itself encountered a number of problems (such as scarce resources, contamination with pathogens, immunoreactions, circulatory disorders, toxicity, and others)—development work has been carried out and is continuing with other oxygen carriers, including those based on perfluorinated hydrocarbons, also known as perfluorocarbons (see for example previously cited references, also Dinkelmann, S., and Northoff, H. (2003) Artificial oxygen carriers—a critical analysis of current developments, Anästhesiologie Intensivmed Notfallmed Schmerzther 38, 47-54 and Spahn, D. R., and Kocian, R. (2005) Artificial $O_2$ carriers: status in 2005. Curr Pharm Des 11, 4099-4114).

Perfluorocarbons readily dissolve respiratory gases such as oxygen and carbon dioxide, and they then release them into cavities, that is to say small hollow areas. They are largely chemically inert, colourless and odourless, and are completely non-corrosive. Their physical properties, such as melting and boiling points, vary—like alkanes—according to the length of the chain or the size, of their carbon skeleton. Their highly inert nature and associated inability to be metabolised, are probably the reason why perfluorocarbons are practically completely non-toxic. Perfluorocarbons are extremely hydrophobic, and also lipophobic. Accordingly, they are used in the related art as artificial oxygen carriers—in conjunction with emulsifiers—in the form of emulsions, and the function of emulsifier is fulfilled for example by synthetic polymers or, most recently, by phospholipids (for example lecithin, occasionally together with cholesterol).

The first experiments with perfluorocarbons as artificial oxygen carriers were conducted as early as the 1960s (see for example Clark, L. C, Jr., and Gollan, F. (1966) Survival of mammals breathing organic liquids equilibrated with oxygen at atmospheric pressure. Science 152, 1755-1756). The basic potential of these compounds for use as oxygen carriers was demonstrated in various experiments, some of which were quite spectacular—mice immersed in perfluorocarbon solutions survived. Major problems associated with the first generation of perfluorocarbon oxygen carriers were the poor stability of the perfluorocarbon emulsions, and side effects associated with the emulsifier used.

The problems were solved by using different perfluorocarbons, such as 1-bromoperfluorooctane (=perfluorooctyl bromide), and lecithin as the emulsifier. Perfluorocarbon preparations of the next generation, such as the preparation Oxygent®, have been used successfully in experiments on animals and clinical studies (see for example Spahn, D. R. (1999) Blood substitutes. Artificial oxygen carriers: perfluorocarbon emulsions. *Crit Care* 3, R93-97).

However, continued clinical use of perfluorocarbons as artificial oxygen carriers is currently limited essentially by two problems, the causes of which are related: the first problem is the relatively short residence time of perfluorocarbons, amounting to just a few hours, in the vascular system; until now, this has enabled perfluorocarbons to be used for short periods, as an interim measure, but has prevented them from being used as a true alternative to blood transfusions. The second problem is the disturbance it creates for the immune system, and the flu-like symptoms associated therewith as well as the risk of increased vulnerability to infection.

The short residence time in the vascular system and the disruption to the immune system are both due to the fact that the emulsion droplets of the perfluorocarbons absorbed by cells of the reticuloendothelial system. This absorption takes place very rapidly, because the system is extremely extensive, and at the same time, while some functions of the cells of the reticuloendothelial system, such as creating inflammation mediators, are activated by absorbing perfluorocarbons, others, such as combating pathogens, are inhibited.

Regarding more comprehensive details about artificial oxygen carriers, particularly as an alternative to blood transfusions and the drawbacks and risks associated therewith, reference is made in particular to Habler, O., Pape, A., Meier, J., and Zwissler, B. (2005) [Artificial oxygen carriers as an alternative to blood transfusion]. *Anaesthesist* 54, 741-754 and to Riess, J. G. (2001) Oxygen carriers ("blood substitutes")—raison d'etre, chemistry, and some physiology. *Chem Rev* 101, 2797-2920.

The object of the present invention is therefore to provide artificial oxygen carriers, preferably based on fluorinated, particularly perfluorinated hydrocarbons, particularly based on perfluorocarbons, which at least to some degree avoid or at least minimise the cited drawbacks of the related art. In particular, such artificial oxygen carriers should be suitable for or capable of being used for example as "blood surrogate" or "blood substitutes" for conditions during and/or after blood loss by the human or animal body (for example following surgical procedures, accidents, injuries, and the like), or for the prophylactic and/or therapeutic treatment of ischaemic conditions or conditions after reperfusion ("tourniquet" or "reperfusion" syndrome).

The applicant has surprisingly discovered that the object as defined, above may be solved by the use of artificial oxygen carriers based on fluorinated, particularly perfluorinated hydrocarbons, preferably perfluorocarbons, wherein the fluorinated hydrocarbons are surrounded, particularly deposited in an oxygen-permeable capsule material, or are enclosed thereby.

BRIEF SUMMARY OF THE INVENTION

The object of the present invention—according to a first aspect of the present invention—is therefore a dispersion of artificial oxygen carriers as described herein; other advantageous refinements of this aspect of the invention are further described.

Another object of the present invention—according to a second aspect of the present invention—is the use of the dispersion according to the invention as described herein; other advantageous refinements of this aspect of the invention are further described.

A further object of the present invention—according to a third aspect of the present invention—is the use of fluorinated, particularly perfluorinated hydrocarbons, preferably perfluorocarbons, as artificial oxygen carriers as described herein; other advantageous refinements of this aspect of the invention are similarly described.

Finally, yet another object of the present invention—according to a fourth aspect of the present invention—is the use of capsules, particularly nanocapsules comprising an oxygen-permeable capsule material and fluorinated, particularly perfluorinated hydrocarbons, preferably perfluorocarbons contained therein and/or enclosed thereby, as artificial oxygen carriers as described herein; other refinements of this aspect are further described.

Naturally, any statements made in the following regarding one of the aspects of the invention also apply correspondingly for the other aspects of the invention, even though no such comment or reference to that effect is made.

DETAILED DESCRIPTION OF THE INVENTION

The object of the present invention—according to a first aspect of the present invention—is thus a dispersion of artificial oxygen carriers that is suitable particularly as a blood substitute, preferably for purposes of transfusion, wherein the dispersion contains capsules with reversible oxygen storage capacity, wherein the capsules comprise an oxygen-permeable capsule material that contains and/or encloses fluorinated, particularly perfluorinated hydrocarbons, preferably perfluorocarbons.

A particular feature of the present invention thus consists in that the fluorinated hydrocarbons that are capable of storing oxygen in reversible manner are available in capsule form, particularly in the form of "nanocapsules". As will be explained in the following, the advantages of the present invention described subsequently have there origin in this One idea that is critical to the present invention is thus the use of capsules, particularly nanocapsules, containing perfluorocarbons, as artificial oxygen carriers.

For the purposes of the capsules, particularly nanocapsules, according to the invention, the term reversible oxygen storage capacity refers particularly to the ability of these capsules to store oxygen until it is discharged or released according to need under physiological conditions, particularly in the body of a human or animal, and particularly into the target tissues where insufficient oxygen is present or ischaemic conditions exist.

The term oxygen storage capacity refers to any kind of storage, for example by physical and/or chemical binding, absorption, inclusion, adsorption, dissolution or similar.

In a preferred manner according to the invention, the capsules, particularly nanocapsules, have the form of "core and shell capsules". In this context, the oxygen-permeable capsule material forms the capsule shell and the fluorinated hydrocarbons are enclosed in and/or surrounded by the oxygen-permeable capsule material, that is to say the fluorinated hydrocarbons form the inside, or the capsule core in these core/shell capsules.

Alternatively, although this is less preferable according to the invention, it is also possible for the capsules, particularly nanocapsules to have the form of matrix capsules. In this case, the oxygen-permeable capsule material forms a matrix and the fluorinated hydrocarbons are deposited and/or enclosed, in the matrix based on this oxygen-permeable capsule material, preferably in homogeneous, even distribution.

Regarding the oxygen-permeable capsule material, particularly the capsule shell of core/shell capsules or the matrix material in the case of matrix capsules, it generally includes or consists of an oxygen-permeable organic polymer. Examples of oxygen-permeable organic polymers that are suitable for the purposes of the invention are in particular poly(lactide-co-glycolides), which may have been derivatized with perfluorinated compounds and/or with polyalkylene (glycol (particularly polyethylene glycol), or polyalkylcyanoacrylates, which may or may not have been fluorinated, and mixtures of these polymers. In particular, derivatization of the polymers listed above may reduce their tendency to aggregate and improve their phagocytic function during application.

According to a particular embodiment, the oxygen-permeable capsule material, particularly the capsule shell of core/shell capsules or the matrix material in the case of matrix capsules may in particular include or consist of an oxygen-permeable organic polymer. In particular, the organic polymer may be obtained or produced by suitable polymerisation processes, particularly emulsion polymerisation, interfacial polymerisation or interfacial precipitation, preferably interfacial polymerisation or interfacial precipitation (for example, production by interfacial precipitation of suitable polymers such as in the production of the aforementioned poly(lactide-co-glycolides), or also for example production by interfacial polymerisation such as is used to produce the aforementioned polyalkylcyanoacrylates). The organic polymer and the capsule shell or capsule matrix produced therefrom preferably contains no sulphur atoms, preferably contains no sulphide bridges, and is particularly free from di- or polysulphide bridges, since these can inhibit oxygen uptake and oxygen transport. It is further preferred if the organic polymer, particularly the capsule shell of core/shell capsules or the matrix material in the case of matrix capsules, has a coherent structure (in contrast for example to capsules whose capsule shell is formed from pure adducts); in this way it is ensured that the oxygen storage and oxygen transport capacity is reliable.

According to a particular embodiment, the oxygen-permeable capsule material, particularly the capsule shell of core/hull capsules or the matrix material of matrix capsules, preferably the particularly oxygen-permeable organic polymer of the capsule shell or matrix, may include modification, particularly surface modification, and/or functional groups. The modification, particularly surface modification, and/or functional groups may in particular be selected from: (i) aggregation inhibiting functional groups, (ii) functional groups that control interaction with biological molecules, (iii) acid functional groups, (iv) hydroxyl groups, (v) preferably anionic groups below the physiological pH, particularly carboxylic acid, sulphate, sulphonate, phosphate and phosphonate groups, (vi) polyalkylene polyol groups, particularly polyethylene glycol groups, (vii) emulsifiers, (viii) dispersing agents and combinations and/or mixtures thereof with each other. In this way, the aggregating properties of the capsules may be controlled and improved dispersibility may be achieved. It is also possible to achieve improved phagocytosis and better oxygen binding and oxygen transfer properties.

It is preferable for the purposes of the invention if the oxygen-permeable capsule material, particularly the capsule shell of core/shell capsules or the matrix material of matrix material is also $CO_2$-permeable.

Regarding the size of the capsules, they should nave a diameter no greater than 7000 nm, particularly no greater than 6500 nm, preferably no greater than 6000 nm; in this way, it is ensured that the capsules are able to pass through the blood vessels, tissues, organs and so on without difficulty. On the other hand, the capsules should have a minimum diameter not less than 5 mm, particularly not less than 10 nm, preferably not less than 20 nm, especially not less than 25 nm, particularly preferably not less than 25 nm, especially preferably not less than 40 nm, most preferably not less than 50 nm, in particular to ensure that storage capacity for sufficient quantities of oxygen is available.

In general, the capsules have a diameter in the range from 5 to 7000 nm, particularly 10 to 6500 nm, preferably 20 to 6000 nm, especially 25 to 5000 nm, particularly preferably 40 to 2500 nm, especially preferably 50 to 1000 nm, even more preferably 50 to 975 nm.

It is particularly preferable for the purposes of the invention if the capsules are provided in the form of nanocapsules, preferably with a core/shell structure. Preferred nanocapsules With a core/shell structure have a diameter in the range from 5 to 7000 nm, particularly 10 to 6500 nm, preferably 20 to 6000 nm, especially 25 to 5000 nm, particularly preferably 40 to 2500 nm, especially preferably 50 to 1000 nm, even more preferably 50 to 975 nm.

The capsules used according to the invention are advantageously exhibit multimodal particle size distribution. In particular in this regard, average diameters D50 of the capsules in the range from 25 to 3000 nm, particularly 50 to 1000 nm, even more preferably 50 to 950 nm, are conceivable.

It is of course evident that one skilled in the art may use different values and ranges from all of the values and ranges cited in the preceding as well as in the remainder of this document depending on the application or individual case, without thereby exceeding the scope of the present invention.

With regard to the weight ratio of oxygen-permeable capsule material to fluorinated hydrocarbons in the capsules, this ratio should be not more than 90:10, particularly not more than 75:10, preferably not more than 50:50. The weight ratio between oxygen-permeable capsule material and fluorinated hydrocarbons in the capsules preferably varies in the range from 90:10 to 1:99, particularly from 80:20 to 5:95, preferably from 75:25 to 10:90, particularly preferably from 70:30 to 15:85. The larger the component of fluorinated hydrocarbons, the greater the oxygen storage capacity, although if the capsule material components are too low the stability of the capsules used according to the invention is no longer assured, which explains the value ranges defined in the preceding.

In general, the capsules used according to the invention have a density from 1.5 to 2.5 g/ml, particularly from 1.8 to 2 g/ml, preferably from 1.85 to 1.9 g/ml.

Although work on developing nanocapsules for medical use generally has been going on intensively for quite some time and nanocapsules are being used or at least have already been suggested as vehicles for various drugs in both therapy and diagnostic applications, nanocapsules have not yet been considered specifically as vehicles for fluorinated hydrocarbons, such as perfluorocarbons, for use as artificial oxygen carriers, particularly for use as a blood surrogate or blood substitute.

In fact, the surprising discovery that it is possible to develop capsules, particularly nanocapsules, with fluorinated hydrocarbons, particularly perfluorocarbons, which are able to be used as artificial oxygen carriers, was only made in the context of the present invention. Such an approach has not been considered previously, because the capsule shell can negatively affect the oxygen transporting property of these substances, resulting in inadequate oxygen storage, transporting and releasing capabilities. Until, now, the use of particulate systems (that is to say capsules) as opposed to emulsions has also militated against such a procedure, particularly with regard to the necessary biological can physiological compatibilities.

However, while working on the present invention it was unexpectedly found that the perfluorocarbon nanocapsules used have similar $O_2$-transporting properties to pure perfluorocarbon emulsions, but—particularly if capsule material is chosen correspondingly—are absorbed by the cells of the reticuloendothelial system significantly less rapidly. As a result, it has surprisingly become possible to avoid or dramatically reduce the problems that limited, the clinical use of perfluorocarbons according to the prior art, particularly the short residence times in the vascular system and disruption to the immune system.

With regard to the fluorinated, particularly perfluorinated, hydrocarbons, preferably perfluorocarbons that are used, they are capable of storing and/or absorbing oxygen reversibly, particularly under physiological conditions, and/or possess the property of being able to store oxygen reversibly, particularly under physiological conditions. By virtue of the reversible nature of their ability to store oxygen, the fluorinated hydrocarbons are able to discharge or release the oxygen again as needed, particularly under physiological conditions, directly at site where it is needed, for example in ischaemic tissues and/or organs.

The fluorinated, particularly perfluorinated hydrocarbons, preferably perfluorocarbons, are preferably in liquid form, particularly under physiological conditions.

The fluorinated, particularly perfluorinated hydrocarbons, preferably perfluorocarbons used according to the invention advantageously have molecular weights in the range from 250 to 2000 g/mol, particularly 300 to 1000 g/mol, preferably 400 to 600 g/mol. In this context, the fluorinated hydrocarbons are preferably in liquid form under normal conditions, particularly ambient temperatures (for example 20° C.) and atmospheric pressure.

In general, perfluorinated particularly perfluorocarbons, are used as the fluorinated hydrocarbons; in this case these are carbon compounds that have been completely substituted with fluorine atoms. However, it is also possible according to the invention to used fluorinated hydrocarbons that contain at least one halogen, other than fluorine, preferably bromine, such as perfluorooctyl bromide.

In general, the fluorinated hydrocarbons used according to the invention are selected from the group of perfluorooctane, perfluorodecane, perfluorodecalin and bromoperfluorooctane and mixtures thereof, particularly perfluorooctane and/or perfluorodecane.

The quantity by volume of capsules in the dispersions according to the invention may vary widely. In general, the dispersions according to the invention contain the capsules in quantities by volume from 1 to 70% by volume, particularly 5% to 65% by volume, preferably 10 to 60% by volume, especially 20 to 50% by volume relative to the dispersions.

The quantity by mass of capsules in the dispersions according to the invention may also vary widely. In general, the dispersions according to the invention contain the capsules in quantities by mass from 5 to 80% by weight, particularly 10 to 75% by weight, preferably 15 to 65% by weight relative to the dispersions.

In order to enable uncomplicated application in the treatment of human or animal bodies, the dispersions according to the invention are generally adjusted to a physiological pH value and/or physiological ionic strength and/or physiological osmolarity and/or physiological ionic composition.

In general, the pH value of the dispersions according to the invention is in the range from 6.5 to 7.9, particularly 7 to 7.5, preferably 7 to 7.45, particularly preferably 7.37 to 7.45, and thus corresponds essentially to the pH value of natural blood and blood plasma.

To adjust and/or maintain the pH value, it may be provided to add a buffer or buffer system, particularly a physiological buffer or a physiological buffer system, preferably phosphate-based.

In order to ensure uncomplicated application, the dispersions according to the invention should have a consistency and viscosity essentially comparable to natural blood or blood serum. In general, the dispersions according to the invention have a specific viscosity $\eta$ in the range from 0.1 to 1.8 s, particularly 0.2 to 1.5 s, preferably 0.25 to 1.25 s, these viscosity values referring particularly to temperatures in the range from 10° C. to 40° C.

The dispersions according to the invention are advantageously in the form of aqueous based dispersions, that is to say the dispersions according to the invention contain water as the continuous phase that is the dispersing agent or dispersant), particularly in the form of a preferably physiological and/or isotonic sodium chloride solution, preferably with a sodium chloride concentration of 0.9% by weight relative to the continuous phase.

With regard to the osmolarity of the dispersion according to the invention, this may also vary widely in general, the dispersions according to the invention have osmolarities in the range from 250 to 350 mOsmol/l, particularly 280 to 310 mOsmol/l.

It may further be provided that the dispersions according to the invention also contain usual auxiliary materials and/or additives, which may particularly be chosen from the group of dispersing aids, emulsifiers, extenders, binders, crosslinking agents, stabilisers, and mixtures thereof. Examples of substances that may be used as emulsifiers include lecithin and/or cholesterol and/or derivatives of bile acids and/or salts of these compounds (for example cholates such as alkali cholates, preferably sodium cholate). However, the quantity of such auxiliary materials and/or additives, particularly the quantity of dispersing aids and/or emulsifiers (for example sodium cholate) in the dispersions according to the invention should advantageously not exceed a concentration of 50 μmol/l, particularly 40 μmol/l, preferably 35 μmol/l. Higher concentrations (such as higher concentrations of emulsifiers) may have a cytotoxic effect and should therefore be avoided.

The present invention thus provides artificial oxygen carriers based on fluorinated hydrocarbons, particularly based on perfluorocarbons, in the form of dispersions of the capsules made from oxygen-permeable capsule material defined previously, and fluorinated hydrocarbons contained therein or enclosed thereby as the actual oxygen carriers (that is to say vehicles for storing oxygen reversibly under physiological conditions), which at least partly avoid, or alleviate the disadvantages of the prior art described in the preceding.

In particular, the artificial oxygen carriers and the dispersions that contain them are suitable for and capable of being used for example as a blood surrogate or blood substitute, particularly in conditions during or after loss of blood in a human or animal body (for example after surgical procedures, accidents, injuries and the like), or for the prophylactic and/or therapeutic treatment of ischaemic conditions or conditions after reperfusion ("tourniquet" or "reperfusion" syndrome).

Within the scope of the present invention, perfluorocarbon nanocapsules may be produced with various capsule materials and surface properties, and with various perfluorocarbons.

The capsules to be used according to the invention, in particular perfluorocarbon (nano)capsules, may be produced in a manner known to one skilled in the art. This may be done for example by in-situ polymerisation of suitable starter monomers, which then form the capsule material or capsule walls, in the presence of the perfluorocarbons to be encapsulated (for example in suitable polymerisation processes, particularly emulsion polymerisation, interfacial polymerisation or similar).

The perfluorocarbon (nano)capsules and the dispersions or pharmaceuticals that contain them are particularly characterized by microscopic and spectroscopic methods, and their biocompatibility, absorption into cells, and ability to transport and deliver oxygen are also verified using laser scanning microscopy and intravital microscopy in simple biological systems, and then in more complex systems up to experimentation on animals.

For the purposes of the present invention, use is made preferably of capsules, particularly nanocapsules with poly(lactide-co-glycolides) possibly modified with perfluorinated compounds and/or polyethylene glycol, or with possibly fluorinated, particularly perfluorinated polyalkylcyanoacrylates as the capsule material, particularly the shell, and perfluorooctane, perfluorodecalin or perfluorodecane as the capsule inside or core, which may be used in the human or animal body as artificial oxygen carriers. In this way, an important basis is provided for an alternative to blood transfusion.

The capsule shell of the perfluorocarbon (nano) capsules used in accordance with the invention, based for example on poly(lactide-co-glycolide) possibly modified with perfluorinated compounds, based on possibly fluorinated polyalkylcyanoacrylate and the like, particularly determines the biological properties, whereas the capsule core, which comprises or consists of perfluorocarbons such as perfluorodecane, perfluorodecalin, perfluorooctane or similar is the actual oxygen carrier.

The perfluorocarbon (nano) capsules provided in accordance with the invention and the dispersions or medications (pharmaceuticals) that contain them enable an extremely wide range of application options. For example, they may be used for all conditions of oxygen starvation in human or animal organisms. Examples of such are damage to cells, tissues and organs caused by ischaemia and reperfusion; typical damage caused by ischaemia and reperfusion are myocardial infarction, stroke, shock conditions following heavy loss of blood, and damage to donor organs during transplant. Mechanisms that have been investigated in this context are disruption to cellular ionic homeostasis in the ischaemic phase (that is to say the phase of oxygen insufficiency that arises when blood circulation is cut off) and the involvement of reactive oxygen and nitrogen species in damage during the reperfusion phase (that is to say when blood circulation is resumed, thus restoring the supply of oxygen, a process that is associated with its own damage component). The perfluorocarbon (nano)capsules provided in accordance with the invention and the dispersions or pharmaceuticals that contain them thus enable for example their use as a protective solution or protective dispersion to protect organs during transplant procedures (of the heart, liver, kidney, lung, pancreas, intestine, or other, for example).

In particular, uniform, storage-stable capsule dispersions of perfluorocarbon (nano)capsules are used in the scope of the present invention. The capsules to be used according to the invention may be produced in known manner, for example by creating an interim miniemulsion, which results in particularly stable dispersions having narrow size distributions. The dependencies between the preparation parameters and the most important properties of the capsule dispersions have been worked out in systematic experiment series using statistical experiment designs. In addition, new characterization methods, based in particular on the use of nuclear magnetic resonance spectroscopy, have been devised in conjunction with the development of the preparation processes.

The choice of capsule shell material may be made particularly on the basis of the following criteria: feasibility and simplicity of production, particularly with regard to large quantities, stability during prolonged storage, permeability for $O_2$ and/or $CO_2$, no existing toxicities, biodegradability, half-life in the vascular system, possibilities for subsequent surface modification, and others.

According to a preferred embodiment for the purposes of the invention, the capsule shell of the perfluorocarbon nanocapsules may be created particularly from poly(lactide-co-glycolide), possibly modified with perfluorinated compounds, or from possibly fluorinated polyalkylcyanoacrylate. If poly(lactide-co-glycolide), possibly modified with perfluorinated compounds is used, the lactide/glycolide ratio may be varied (for example in the range from 25:75 to 75:25). The perfluorocarbons that may be used advantageously for the purpose of the invention are perfluorodecane, perfluorodecalin and perfluorooctane.

Poly(lactide-co-glycolide)-perfluorocarbon (nano) capsules preferably used according to the invention may be produced for example as follows: the poly(lactide-co-glycolide) represents a polymer that is constructed in sequentially randomised manner from lactyl units (—CH(CH$_3$)—CO—O—) and glycolyl units (—CH$_2$—CO—O—) in variable quantity ratios (see for example Wang, L., Venkatraman, S., Gan, L. H., and Kleiner, L. (2005), Structure formation in injectable poly(lactide-co-glycolide) depots. II. Nature of the gel. J Biomed Mater Res B Appl Biomater 72, 215-222). The various poly(lactide-co-glycolide) polymers differ both with respect to their content of lactyl units (for example 50% to 85%), and in terms of variable viscosity with a given lactyl content. All poly(lactide-co-glycolide) polymers are ultimately reduced to water and $CO_2$ in mammals. They thus do not present a health risk in physiological terms and as such have been used in pharmacology for almost forty years. The walls of these capsules are highly porous and thus readily permeable for $O_2$ and $CO_2$. Encapsulation results in absolutely no loss of functionality. The capsules may be produced for example in similar manner to the production process described for example by Pisani, E., Tsapis, N., Paris, J., Nicolas, V., Cattel, L., and Fattal, E. (2006) Polymeric nano/microcapsules of liquid Perfluorcarbons for ultrasonic imaging: physical characterization. *Langmuir* 22, 4397-4402. The process described there may be used correspondingly for encapsulation of perfluorocarbons according to the invention, particularly in order to produce nanocapsules as oxygen carriers, for example with cores of perfluorooctane, perfluorodecalin or perfluorodecane. The poly(lactide-co-glycolide) may or may not be modified or derivatized with perfluorinated compounds.

Equally preferred for the purposes of the invention are possibly fluorinated polyalkylcyanoacrylate-perfluorocarbon (nano)capsules. As a reactive monomer, alkylcyanoacrylate offers the advantage that it can be polymerised to form capsules under extremely gentle conditions at the interface of an oil-in-water emulsion (see for example Couvreur, P. Kante, B., Roland, M., Guiot, P., Bauduin, P., and Speiser, P. (1979) Polycyanoacrylate nanocapsules as potential lysosomotropic carriers: preparation, morphological and sorptive properties. *J Pharm Pharmacol* 31, 331-332 and Florence, A. T., Whateley, T. L., and Wood, D. A. (1979) Potentially biodegradable microcapsules with poly(alkyl 2-cyanoacrylate)membranes. *J Pharm Pharmacol* 31, 422-42). In this context, anionic polymerisation may be initiated by making a controlled change to the ph value of the aqueous phase, resulting in a physically cross-linked, but relatively porous and gas-permeable polymer shell. A number of variants on the preparation of polyalkylcyanoacrylate (nano)capsules have now been described and the process is even possible for larger scale production (see for example Wohlgemuth, M. Machtle, W., and Mayer, C. (2000) Improved preparation and physical studies of polybutylcyanoacrylate nanocapsules. *J Microencapsul* 17, 437-448; Mayer, C. (2005) Nanocapsules as drug delivery systems. *Int J Artif Organs* 28, 1163-1171; Altinbas, N., Fehmer, C, Terheiden, A., Shukla, A., Rehage, H., and Mayer, C. (2006) Alkylcyanoacrylate nanocapsules prepared from mini-emulsions: a comparison with the conventional approach. *J Microencapsul* 23, 567-581; Al Khouri Fallouh, N., Roblet-Treupel, L., Fessi, H., Devissaguet, J. P., and Puisieux, F. (1986) Development of a new process for the manufacture of polyisobutylcyanoacrylate nanocapsules. *Int J Pharm* 28, 125-132; Lescure, F., Zimmer, C., Roy, D., and Couvreur, P. (1992) Optimization of polyalkylcyanoacrylate nanoparticle preparation—Influence of sulfur-dioxide and pH on nanoparticle characteristics. *J Colloid Interface Sci* 154, 77-86). Particularly for producing fluorinated polyalkylcyanoacrylate nanocapsules, a process may be followed in which alkylcyanoacrylate (for example ethylcyanoacrylate) is first converted to fluorinated alkylcyanoacrylate by transesterification, and this is then transformed into capsules having a fluorinated alkylcyanoacrylate shell with a perfluorocarbon capsule core contained therein for example by interfacial polymerisation about dispersed droplets of the perfluorocarbon (for example perfluorodecalin).

The capsules used according to the invention are mechanically and thermally stable, and may be stored practically indefinitely either as a dispersion or in a freeze-dried condition. Smaller molecules such as ethanol or benzene undergo rapid exchange through the capsule shell, their half-life in the encapsulated condition is in the order or just a few milliseconds. The diameters of the capsules are in the nanometer to micrometer range (for example between 100 and 500 nm) and they may be controlled via the limit conditions of the preparation. The polymer is biodegradable, the by-products of decomposition are of extremely low toxicity, if at all. Polyalkylcyanoacrylate nanocapsules are thus versatile and adaptable carrier systems for the present invention. Dispersions of polyalkylcyanoacrylate nanocapsules may be stabilised using amphiphilic block copolymers. In order to achieve longer cycle times in the living organism, they may also be stabilised using chitosan, which results in positively charged capsules. The particular advantage of polyalkylcyanoacrylate nanocapsules over other biodegradable systems is mainly represented by the relatively long life cycle of the capsules under physiological conditions.

Another object of the present invention—according to a second aspect of the present invention—is the use of the dispersions according to the present invention described in the preceding for the prophylactic and/or therapeutic treatment of oxygen starvation conditions in the bodies of humans and animals and for the production of a medication for the prophylactic and/or therapeutic treatment of oxygen starvation conditions in the bodies of humans and animals.

The concept of the condition of oxygen starvation in a human or animal body as it is used for the purpose of the present invention refers particularly to ischaemic and hypoxic conditions in the human or animal body and/or in certain tissues or organs, and for the purpose of the present invention the term ischaemia is used particularly to mean reduced or failed blood flow to a tissue organ (for example the condition following blood loss, haemorrhaging, and the like), which is accompanied by oxygen starvation of the site concerned (as a result of which cellular metabolism is suppressed or ultimately even fails altogether), while the term hypoxy for the purposes of the present invention is used specifically to describe the state of oxygen starvation in tissue (for example the condition after gas poisoning, such as poisoning with carbon monoxide, and similar) (and it should be noted that complete absence of oxygen is also referred to as anoxia).

A further object of the present invention is the use of dispersions according to the invention described in the preceding as blood substitutes, particularly for the purposes of transfusions.

The dispersions according to the invention may be used for example for the prophylactic and/or therapeutic treatment of conditions of the human or animal body during and/or after loss of blood, such as may occur particularly during surgical procedures, accidents, injuries or the like.

The dispersions according to the invention may also be used just as well for the prophylactic and/or therapeutic treatment of ischaemic conditions or conditions following reperfusion, particularly the tourniquet syndrome (reperfusion syndrome), and/or to produce a drug for the prophylactic and/or therapeutic treatment of ischaemic conditions or conditions following reperfusion, particularly the tourniquet syndrome (reperfusion syndrome).

The dispersions according to the invention may also be used to protect organs during transplant operations. In this way for example it is possible to provide effective protection for organs that have been removed and/or are to be transplanted until they are implanted in the recipient's body (for example by perfusion with the dispersion according to the invention).

The dispersions according to the invention may also be used for the prophylactic and/or therapeutic treatment of gas bubble formation or gas embolisms in the bloodstream of the human or animal body and/or to produce a medication for the prophylactic and/or therapeutic treatment of gas bubble formations in the bloodstream or gas embolisms in the human or animal body (for example for treating gas embolisms such as may occur as a consequence of incorrect diving procedures in recreational diving). In this instance, the good gas dissolving properties (with regard to oxygen, carbon dioxide, nitrogen and such) of the dispersions according to the invention and the capsules they contain are particularly valuable.

The dispersions according to the invention may also be used with heart/lung machines, particularly for the prophylactic and/or therapeutic treatment of gas embolisms in the human or animal body and/or to produce a medication for the prophylactic and/or therapeutic treatment of gas embolisms in the human or animal body. This may serve for example as an efficient way to prevent brain damage as a result of oxygen starvation conditions.

In the same way, the dispersions according to the invention may also be used for the prophylactic and/or therapeutic treatment of incidents of gas or smoke poisoning in the human or animal body and/or to produce a medication for the prophylactic and/or therapeutic treatment of gas or smoke poisoning in the human or animal body (for example in the case of smoke poisoning as a consequence of a fire, or also in the case of gas poisoning, such as carbon monoxide or hydrogen cyanide gas poisoning or similar).

In the uses according to the invention described above and in the following, the dispersions according to the invention may be applied particularly in quantities from 5 to 15,000 ml, particularly from 5 to 10,000 ml, preferably from 10 to 3000 ml per single dose, preferably by transfusion.

A further object of the present invention—according to a third aspect of the present invention—is the use of fluorinated, particularly perfluorinated hydrocarbons, preferably perfluorocarbons, as artificial oxygen carriers for the prophylactic and/or therapeutic treatment of the human or animal body, particularly as a blood substitute, preferably for transfusion purposes, wherein the fluorinated hydrocarbons are applied in the form of capsules with reversible oxygen storage capacity, wherein the capsules comprise an oxygen-permeable capsule material that contains and/or encloses the fluorinated hydrocarbons. With regard to this aspect of the invention, the capsules may particularly be applied or used in the form of a dispersion, particularly as described in the preceding. In particular, the capsules described previously may be used for the prophylactic and/or therapeutic treatment of oxygen starvation conditions in the human or animal body and/or to produce a medication for the prophylactic and/or therapeutic treatment of oxygen starvation conditions in the human or animal body. The capsule systems described previously may particularly be used for prophylactic and/or therapeutic treatment of conditions in the human or animal body during and/or after blood loss, particularly such as is associated with surgical procedures, accidents, injuries or the like. It is also conceivable to use the capsule systems described previously for the prophylactic and/or therapeutic treatment of ischaemic conditions or conditions following reperfusion, particularly the tourniquet syndrome (reperfusion syndrome). It is also conceivable to use them to protect organs during transplant procedures, as described in the aforegoing. The capsules described in the preceding may also be considered for use in the prophylactic and/or therapeutic treatment of gas bubble formation or gas embolisms in the human or animal bloodstream and/or to produce a medication for the prophylactic and/or therapeutic treatment of gas bubble formation or gas embolisms in the human or animal bloodstream.

This also includes use of the capsules described in the preceding with heart/lung machines, particularly for the prophylactic and/or therapeutic treatment of gas embolisms in the human or animal body and/or to produce a medication for the prophylactic and/or therapeutic treatment of gas embolisms in the human or animal body. Finally, it is also conceivable for the capsules described in the preceding to be used for the prophylactic and/or therapeutic treatment of gas or smoke poisoning in the human or animal body and/or to produce a medication for the prophylactic and/or therapeutic treatment of cases of gas or smoke poisoning in the human or animal body.

Finally, a further object of the present invention—according to a fourth aspect or the present invention—is the use of capsules, particularly nanocapsules, having an oxygen-permeable capsule material and fluorinated, particularly perfluorinated hydrocarbons, preferably perfluorocarbons contained therein and/or enclosed thereby, As artificial oxygen carriers, particularly as a blood substitute, particularly for the purposes and therapies cited previously (for example for protecting organs during transplant operations and/or to protect organs to be transplanted, particularly in the period between removal and implantation of the organ, and similar).

In order to avoid unnecessary repetition, for the purpose of additional details about the other inventive aspects of the present invention, reference is herewith made to the preceding notes regarding the first inventive aspect, which apply correspondingly for all other aspects of the invention.

Further configurations, adaptations and variations of the present invention will be easily evident and feasible to one skilled in the art upon reading the description without exceeding the scope of the present invention.

The following embodiments serve purely to illustrate the present invention, and the present invention shall in no way be limited thereto.

EMBODIMENTS

Production of Perfluorocarbon (Nano)Capsules Usable According to the Invention

Instruction for synthesising poly(D, L-lactide-co-glycolide) capsules having a diameter of (2.5±1.5) μm and other capsule systems according to the invention Poly(D,L-lactide-co-glycolide) (100 mg) having an internal density of about 0.45 to 0.6 g/cm$^3$ and fluorodecalin (100 μl) are dissolved in dichloromethane (6 ml) at room temperature. Sodium cholate (1.5%) is dissolved in distilled water, and this solution is then cooled to 4° C. The dichloromethane solution (6 ml) is then stirred vigorously to mix with the cold, aqueous sodium cholate solution (20 ml) in an ice bath. An Ultraturrax equipped with distribution adapter (Ultraturrax T25/SN-25-10G manufactured by IKA, stirring speed 13,500 rpm, stirring duration 2 minutes) is used for stirring. To enable visualisation and characterization, capsules can also be produced in which the capsule material is enriched with Nile Red fluorescent stain. These capsules are produced similarly, by pipetting 150 μl of a concentrated Nile Red solution (0.057 mg/ml in dichloromethane) into the dichloromethane solution (6 ml) that contains the poly(D,L-lactide-co-glycolide) and the fluorodecalin. In all cases, the dichloromethane phase is removed after stirring by flushing the two-phase reagent mixture (approx. 26 ml) with a small oxygen gasflux (0.1 to 100 ml/min) until the organic phase has been completely driven off. The capsules settle slowly ($t_{1/2}$ about 6 hours) in the highly concentrated cholate solution and may then be separated and absorbed in a 0.9% NaCl solution for transfer to dispersions according to the invention for appropriate use ("blood surrogate" or "blood substitute") (Application quantities: 5 to 15,000 ml, particularly 5 to 10,000 ml, preferably 10 to 3000 ml).

Perfluorocarbon (nano)capsules usable according to the invention and having various ratios in the poly(D,L-lactide-co-glycolide) in the range from 25:75 to 75:25 and with variable inner densities of the capsules from 0.16 to 1.3 dl/g are produced in subsequent synthesis steps.

Perfluorocarbon (nano)capsules usable according to the invention are also prepared correspondingly with a capsule shell based on poly(D,L-lactide-co-glycolide) and derivatized with perfluorinated compounds, as well as perfluorocarbon (nano)capsules having a capsule shell based on poly(D, L-lactide-co-glycolide) and derivatized with polyethylene glycol.

To synthesise modified poly(D,L-lactide-co-glycolide) capsules, for example having a diameter of (2.5±1.5) μM the following procedure may be carried out for example: poly(D, L-lactide-co-glycolide) (50:50, 92 mg) having terminal carboxyl groups and an internal density of 0.45 to 0.6 dl/g is dissolved in dichloromethane (3 ml) at room temperature. A second poly(D,L-lactide-co-glycolide) (50:50, 8 mg), which forms an 85:15 copolymer with a 5000 Dalton polyethylene glycol, is also dissolved in dichloromethane (3 ml) at room temperature. After the polymer dissolving process is complete, the two solutions are combined. Then fluorodecalin (100 µl) is dissolved in this dichloromethane solution (6 ml). Sodium cholate (1.5%) is dissolved in distilled water, and this solution is then cooled to 4° C. The dichloromethane solution (6 ml) is then mixed with the cold, aqueous sodium cholate solution (20 ml) while stirring vigorously in an ice bath. An Ultraturrax equipped with a distribution adapter (for example Ultraturrax T25/S-25KV-25G-IL manufactured by IKA, stirring speed 6000 rpm, stirring duration 2 minutes) is used for stirring.

To enable visualisation and characterization, capsules can also be produced in which the capsule material is enriched with Nile Red fluorescent stain. These capsules are produced similarly, by pipetting 150 µl of a concentrated Nile Red solution (0.057 mg/ml in dichloromethane) into the dichloromethane solution (6 ml) that contains the poly(D,L-lactide-co-glycolide)/fluorodecalin. In all cases, the dichloromethane phase is removed after stirring by flushing the two-phase reagent mixture (approx. 26 ml) with a small oxygen gasflux (0.1 to 1 ml/min) until the organic phase has been completely driven off. The capsules settle slowly ($t_{1/2}$ about 6 hours) in the highly concentrated cholate solution and may then be separated and absorbed in a 0.9% NaCl solution. An improvement in terms of avoiding aggregation and phagocytosis may be achieved particularly by derivatization of the polymers.

Perfluorocarbon (nano)capsules usable according to the invention are also prepared having a capsule shell based on alkylcyanoacrylate or on perfluoroalkyl cyanoacrylate.

Physical-chemical characterization of the perfluorocarbon (nano) capsules usable according to the invention and the dispersions containing them The perfluorocarbon nanocapsules usable according to the invention are characterized in terms of their size, homogeneous structure, configuration and composition by the following methods:

Confocal Laser Scanning Microscopy (LSM)

Confocal Laser Scanning Microscopy (LSM) is used to determine the size and demonstrate the homogeneous structure of the perfluorocarbon nanocapsules usable according to the invention. For this, the nanocapsules are stained with Nile Red fluorescent stain (9-Diethylamino-5H-benzo[α]phenoxazine-5-one), which accumulated in the capsule wall because of its lipophilic properties. The LSM measurements are taken using a helium/neon laser and high-resolution lenses. Aliquots of stained perfluorocarbon nanocapsules and perfluorocarbon nanocapsules diluted with a physiological buffer are deposited in modified Pentz chambers on the surface of slides that have been treated with poly-L-lysine and the fluorescence is displayed in various focal planes of the liquid column. Because the film thickness of the confocal system is optically very small, it is also possible to show a small number of spatial representations of the perfluorocarbon nanocapsules. Their size and homogeneity is quantified on the basis of the signals detected using the corresponding "Physiology Evaluation" software of the LSM 510 system.

Light-microscopic observation of the dispersed capsules in the dark field Laser Scanning Microscopy is only of limited use for determining the size of nanocapsules having a diameter smaller than 1 µm. Therefore, the additional method of light-microscopic observation, of the dispersed capsules in the dark field is also carried out. Light-microscopic observation of the dispersed capsules in the dark field is used to determine the Brownian motion of the particles. In this procedure, the movements of individual particles are evaluated by automatic image analysis of a video file that is generated in real time and processed to yield a capsule size histogram.

Scanning probe microscopy (AFM) Scanning probe microscopy employs a method with which it is possible not only to capture an image of the capsules, but also to determine their mechanical properties. In a compression test, a force path diagram is plotted that yields important data about the mechanical strength, elastic deformability and elasticity of the capsules. The way in which the capsule shell folds after the compression test also enables conclusions to be drawn regarding the thickness of the capsule membrane and the internal structure of the capsules.

$^{13}$C and $^{19}$F NMR spectroscopy Nuclear magnetic resonance measurements of carbon atoms by observing the $^{13}$C isotope assist with the chemical characterization of the capsule wall and return information about the progress of the polymerisation reaction. In addition, measurements of the fluorine atoms using pulsed field gradients provide information about the self-diffusion properties of the fluorinated hydrocarbon, which in turn allows conclusions to be made about the phase condition and phase homogeneity of the capsule content. In this way, for example, it is ensured that the liquid content is located in a free cavity and not in a spongy-porous medium, for example. Recording of $^{19}$F line spectra also enables oxygen uptake to be observed: the paramagnetic properties of oxygen affect the resonance signal of the fluorine atoms, yielding typical line widening effects and shortened relaxation times, and the nature of these enables conclusions to be drawn regarding the concentration of oxygen inside the capsules. In this way, it is possible to determine both the kinetics of the oxygen absorption and the position of the distribution equilibrium.

The following table shows the parameters of the capsules that have been created and characterized, and thus also of the dispersions that contain them:

| Parameters | Values |
| --- | --- |
| Capsule density | 1.80-1.95 g/ml |
| Concentration of capsules | 5-60% by vol. |
| Size of capsules | 50-5000 nm |
| Specfic solution viscosity n | 0.25-1.25 s |
| pH value of dispersions | 7.00-7.45 |
| Ionic strength of dispersions | 280-310 mOsmo 1/1 |
| Capsule materials (material of the capsule shell) | A: Alkylcyanoacrrylate<br>B: Perfluoroalkyl cyanoacrylate<br>C: Poly (D, L-lactide-co-glycolide)<br>D: Poly (D, L-lactide-co-glycolide) derivatized with perfluorinated compounds<br>E: Poly (D, L-lactide-co-glycolide) derivatized with polyethylene glycol |
| Perfluorocarbons | Perfluorodecalin<br>Perfluorooctane<br>Perfluorodecane |
| Quantity used | 5 to 15,000 ml, particularly 5 to 10,000 ml, preferably 10 to 3000 ml |

Testing of biocompatibility of perfluorocarbon nanocapsules, their absorption into cells and capacity to transport and deliver oxygen in simple biological systems Possible cytotoxic effects of the perfluorocarbon nanocapsules, their absorption in the cells and activation/deactivation of the cells due to contact with the perfluorocarbon nanocapsules are investigated using recognised techniques on cultivated macrophages and endothelial cells, that is to say cells of the reticuloendothelial system. Among the methods used to detect the cytotoxic effect of the perfluorocarbon nanocapsules and their absorption into the cells is laser scanning microscopy. The possible cytotoxic effect of the perfluorocarbon nanocapsules and their absorption into cells is also studied in rat livers that have been perfused in vivo. To detect uptake of the nanocapsules (marked with fluorescing Nile Red) in the cells of the intact organism, intravital microscopy is used. The capability of perfluorocarbon nanocapsules to transport and oxygen and supply it to tissues is also examined comparatively in in vivo perfused rat livers. Since oxygen is only poorly soluble in aqueous phases, the usual perfusion of Krebs-Henseleit buffer saturated with carbogen (95% $O_2$, 5% $CO_2$) must be made in high volumes (30 ml/min) to ensure delivery of adequate oxygen. In experiments with perfluorocarbon nanocapsules and perfluorocarbon emulsions or perfluorocarbon dispersions, it is confirmed that (compared with the Krebs-Henseleit buffer) the flowthrough rate may be reduced significantly before ischaemic tissue damage occurs, and that a physiological flow rate is achievable.

The invention claimed is:

1. A capsule dispersion of artificial oxygen carriers for use as a blood substitute, wherein the dispersion contains capsules with reversible oxygen storage capacity, wherein the capsules comprise an oxygen-permeable capsule material that contains or encloses fluorinated hydrocarbons,
   wherein the capsule dispersion is storage stable and the capsules have a diameter in the range of 50 to 1,000 nm,
   wherein the oxygen-permeable capsule material comprises an oxygen-permeable organic polymer, wherein the polymer is selected from the group of poly(lactide-co-glycolides) and polyalkylcyanoacrylates and mixtures thereof
   wherein the oxygen-permeable capsule material contains no sulphide bridges and has a coherent structure,
   wherein the weight ratio of oxygen-permeable capsule material to fluorinated hydrocarbons in the capsules is in the range of from 75:25 to 10:90,
   wherein the fluorinated hydrocarbons have molecular weights in the range from 250 to 2000 g/mole and are in liquid form,
   wherein the dispersion contains the capsules in volume-related quantities from 1-70% by volume relative to the dispersion,
   wherein the dispersion is adjusted to a physiological pH value,
   wherein the dispersion has a specific viscosity $\eta$ in the range from 0.1 to 1.8 relative to temperatures in the range from 10° C. to 40° C., and
   wherein the dispersion is an aqueous-based dispersion and contains water as the continuous phase in the form of a physiological and isotonic sodium chloride solution.

2. The dispersion as defined in claim 1, wherein the capsules are constructed as core/shell capsules, wherein the oxygen-permeable capsule material forms the capsule shell and wherein the fluorinated hydrocarbons are enclosed by the oxygen-permeable capsule shell.

3. The dispersion as defined in claim 1, wherein the capsules are in the form of matrix capsules, wherein the oxygen-permeable capsule material forms a matrix and the fluorinated hydrocarbons are deposited in the matrix based on the oxygen-permeable capsule material.

4. The dispersion as defined in claim 1, wherein the oxygen-permeable organic polymer is derivatized with perfluorinated compounds and/or with polyakylene glycol, polyalkylcyanoacrylates, fluorinated polyalkylcyanoacrylates and mixtures thereof.

5. The dispersion as defined in claim 1, wherein the oxygen-permeable capsule material comprises an oxygen-permeable organic polymer, wherein the organic polymer is obtained by emulsion polymerisation, interfacial polymerisation or interfacial precipitation and wherein the organic polymer contains no di- or polysulphide bridges.

6. The dispersion as defined in claim 1, wherein the oxygen-permeable capsule material includes a modification and/or functional groups, wherein the modification and/or functional groups is/are selected from (i) aggregation inhibiting functional groups, (ii) functional groups that control interaction with biological molecules, (iii) acid functional groups, (iv) hydroxyl groups, (v) anionic groups below the physiological pH, carboxylic acid, sulphate, sulphonate, phosphate and phosphonate groups, (vi) polyalkylene polyol groups and polyethylene glycol groups, (vii) emulsifiers, (viii) dispersing agents and combinations and mixtures thereof with each other.

7. The dispersion as defined in claim 1, wherein the oxygen-permeable capsule material is also $CO_2$-permeable.

8. The dispersion as defined in claim 1, wherein the capsules have a density from 1.5 to 2.5 g/ml.

9. The dispersion as defined in claim 1, wherein the fluorinated hydrocarbons contain at least one halogen other than fluorine or wherein the fluorinated hydrocarbons are selected from the group of perfluorooctane, perfluorodecane, perfluorodecalin and bromoperfluorooctane and mixtures thereof.

10. The dispersion as defined in claim 1, wherein the dispersion contains the capsules in mass-related quantities from 5 to 80% by weight.

11. The dispersion as defined in claim 1, wherein the dispersion is adjusted to a physiological ionic strength and a physiological osmolarity and a physiological ionic composition.

12. The dispersion as defined in claim 1, wherein the dispersion is adjusted to a pH value in the range from 6.5 to 7.9 and wherein the dispersion contains a physiological buffer.

13. The dispersion as defined in claim 1, wherein the dispersion has an osmolarity in the range from 250 to 350 mOsmol/l.

14. The dispersion as defined in claim 1, wherein the dispersion has a sodium chloride concentration of 0.9% by weight relative to the continuous phase.

15. A method of treating a human suffering from oxygen deficiency conditions of the human or animal body, the method comprising administering a pharmaceutically efficient amount of the dispersion as defined in claim 1.

* * * * *